(12) United States Patent
Lohmann et al.

(10) Patent No.: US 6,169,127 B1
(45) Date of Patent: Jan. 2, 2001

(54) PLASMA-INDUCED POLYMER COATINGS

(75) Inventors: Dieter Lohmann, Münchenstein; Peter Chabrecek, Basel, both of (CH); Jens Höpken, Lörrach (DE)

(73) Assignee: Novartis AG, Basel (CH)

( * ) Notice: Under 35 U.S.C. 154(b), the term of this patent shall be extended for 0 days.

(21) Appl. No.: 09/077,505

(22) PCT Filed: Feb. 12, 1996

(86) PCT No.: PCT/EP96/05326

§ 371 Date: Jun. 2, 1998

§ 102(e) Date: Jun. 2, 1998

(87) PCT Pub. No.: WO97/21497

PCT Pub. Date: Jun. 19, 1997

(30) Foreign Application Priority Data

Aug. 30, 1996 (EP) .................................................. 96810643

(51) Int. Cl.[7] ................ G02C 7/04; C08J 7/18; C08L 39/06
(52) U.S. Cl. .................. 523/106; 427/488; 427/491; 523/105; 523/108; 351/159; 524/548
(58) Field of Search ..................................... 427/488, 491; 523/105, 106, 108; 524/548; 351/159

(56) References Cited

U.S. PATENT DOCUMENTS 5,007,928 * 4/1991 Okamura et al. .
5,013,338   5/1991 Anand et al. ......................... 55/158
5,153,072 * 10/1992 Ratner et al. .

FOREIGN PATENT DOCUMENTS

WO 92/02114   7/1991 (WO) .

OTHER PUBLICATIONS

Growth of Fluorocarbon Polymer Thin Films with High CF2 fractions and Low Dangling Bond Concentrations by Terhman Chemical Vapor Deposition, Limb, Scott J., et al, Applied Phys. Lett, 68 (20, May 13, 1996.
International Search Report (Jul. 4, 1997).

* cited by examiner

Primary Examiner—Peter A. Szekely
(74) Attorney, Agent, or Firm—R. Scott Meece; Robert J. Gorman, Jr.

(57) ABSTRACT

The present invention relates to coated particles wherein the polymer chains of the coating are obtainable by after-glow plasma induced polymerization of a monomer under special plasma conditions. The invention further relates to a method for the production of articles coated with a polymer having these features.

15 Claims, No Drawings

PLASMA-INDUCED POLYMER COATINGS

The present invention relates to coated articles wherein the coating comprises a polymer having desirable characteristics regarding adherence to the substrate, durability, wettability, biocompatibility and permeability. More particularly, the present invention relates to an article, such as a biomedical material or article, especially a contact lens, including an extended-wear contact lens which is at least partially coated with a polymer obtainable by after-glow plasma-induced polymerization of a polymerizable unsaturated compound, preferably a polymerizable vinyl or isopropenyl compound under specific plasma conditions. The invention further relates to a method for the production of articles coated with a polymer of said features.

The provision of a coating on a substrate may generally be desirable for a variety of reasons including protection of the substrate and provision of desirable surface characteristics which the substrate material does not exhibit to the required degree. In the case of biomedical devices, such as ophthalmic devices, e.g. contact lenses it is desirable to have surfaces which are readily wettable by an aqueous liquid such as tear fluid and are capable to retain an aqueous fluid layer which is beneficial for the comfort of the wearer. The sliding motion of the contact lens is facilitated by the presence of a continuous layer of tear fluid on the contact lens, a layer which lubricates the tissue/lens interface. Additionally, the adhesiveness towards proteins, lipids, minerals, cell debris and other spoilations or microorganisms, the permeability and stability characteristics of the surface of the contact lens having a coating thereon are of great importance. The permeability of the lens material for gases, water and ions which are required especially in the case of extended wear contact lenses, preferably must not be impaired by the coating which is provided in order to impart hydrophilicity to the surface, and the coating should exhibit thermal, oxidative and hydrolytic stability as well as resistance to formation of deposits from tear components and delamination caused by mechanical stress.

A variety of different types of processes for preparing polymeric coatings on a substrate have been disclosed in the prior art. Coatings can be prepared on the surface of a substrate by any of the classical polymerization methods including bulk polymerization, deposition of polymerizing material from the vapour phase and coating of the substrate surface with a layer of a polymerizable monomer and polymerizing said monomer on the surface of the substrate. Representative for the prior art disclosing preparation of coatings on substrates using classical "wet" chemistry EP-A-632 329 should be mentioned, which describes functionalized photoinitiators which may be bound to an inorganic or organic substrate. One embodiment of said disclosure relates to a contact lens which comprises a thin outer polymer layer on the layer of the photoinitiator which is obtainable by applying a thin coating of photopolymerizable ethylenically unsaturated substances on the surface of the substrate carrying photoinitiator groups and polymerization of the layer of ethylenically unsaturated substances by irradiation.

With these methods using classical "wet" chemistry, however, it is not always possible to obtain the desired coating characteristics, for example resistance to delamination, stability and permeability characteristics which are necessary for the surface of biomedical devices including contact lenses.

A method for preparing polymeric coatings, especially thin coatings on a variety of substrates which is substantially different from the wet chemical methods is the polymerization of polymerizable unsaturated or saturated compounds under the effect of a plasma generated by electric discharge. Plasma-induced polymerization is a physical method of modifying surfaces by depositing a polymer on the surface in a way which is basically dry and without direct contact of the substrate with a solution of the material to be coated. The term "plasma" denotes an ionized gas, e.g. created by electric glow discharge which may be composed of electrons, ions of either polarity, gas atoms and molecules in the ground or any higher state of any form of excitation, as well as of photons. It is often called "low temperature plasma". For a review of plasma polymerization and its uses reference is made to R. Hartmann "Plasmapolymerisation: Grundlagen, Technik und Anwendung, Jahrb. Oberflächentechnik (1993) 49, pp. 283–296, Battelle-Inst. e.V. Frankfurt/Main Germany; H. Yasuda, "Glow Discharge Polymerization", Journal of Polymer Science: Macromolecular Reviews, vol. 16 (1981), pp. 199–293; H. Yasuda, "Plasma Polymerization", Academic Press, Inc. (1985); Frank Jansen, "Plasma Deposition Processes", in "Plasma Deposited Thin Films", ed. by T. Mort and F. Jansen, CRC Press Boca Raton (19); O. Auciello et al. (ed.) "Plasma-Surface Interactions and Processing of Materials" publ. by Kluwer Academic Publishers in NATO ASI Series; Series E: Applied Sciences, vol. 176 (1990), pp. 377–399; and N. Dilsiz and G. Akovali "Plasma Polymerization of Selected Organic Compounds", Polymer, vol. 37 (1996) pp. 333–341.

For plasma polymerization to produce a coating on a substrate which may also be called "plasma grafting", "plasma deposition" or "plasma coating" a suitable organic monomer or a mixture of monomers having polymerizable unsaturated groups is introduced into the plasma zone of the reactor where it is fragmented and/or activated forming further excited species in addition to the complex mixture of the activated plasma gases. The excited species and fragments of the monomer recombine upon contact with the substrate in an undefined way to a largely undefined structure which contains a complex variety of different groups and chemical bonds forming a highly crosslinked polymer deposit on the substrate. If $O_2$, $N_2$ or oxygen or nitrogen containing molecules are present, either within the plasma reactor during the plasma coating process, or on exposure of the plasma coated substrate to oxygen or air subsequent to the plasma process the polymeric deposit will include a variety of polar groups.

In this technique, which is called in the following "in-glow" plasma polymerization the substrate may be located within the plasma zone or alternatively outside (below) the plasma zone and the monomer(s) as well as the plasma gas stream (e.g. $H_2$, He, Ar) are introduced into the plasma zone. With respect to the preparation of coatings on contact lenses using in-glow plasma polymerization U.S. Pat. No. 4,312,575 discloses a soft corneal contact lens comprising a soft, highly oxygen-permeable polymeric lens having formed on the surface thereof an ultrathin optically clear, impermeable barrier coating which is tightly cross-linked and comprises the reaction product resulting from an electrical glow discharge polymerization process. JP-A-62/031803 discloses plasma polymerization of a mixture of oxygen and a saturated hydrocarbon to form a thin film on the surface of optical parts, e.g. contact lenses. U.S. Pat. No. 4,783,374 discloses an ophthalmic lens having an abrasion resistant transparent coating which comprises a plasma assisted chemical vapor-deposition deposited alkene-silane plasma reaction product of a silane, an alkene and an oxygen source. JP-A-60/163901 discloses the plasma polymerization of mixtures of unsaturated hydrocarbons and oxygen to form thin hydrophilic films on contact lenses. Plasma deposition of an ultra thin layer of a polymer of acetylene-$H_2O$—$N_2$ onto poly(methylmeth-acrylate) contact lenses is disclosed by H. Yasuda et al. in J. Biomed. Mater. Res. (1975), pp. 629–643. EP-A-152 256 discloses an optical product having a thin film on its surface which is obtained by subjecting a mixed gas of oxygen and a hydrocarbon compound having a double bond to plasma polymerization. U.S. Pat. No. 5,260,093, U.S. Pat. No. 5,326,584, WO-A-94/11118 and U.S. Pat. No. 5,080,924 disclose a method of permanently modifying the surface of a substrate material such as an intraocular lens so as to develop a microscopically smooth, biocompatible surface thereon by covalently grafting a biocompatible polymeric material to the surface of the substrate by radio frequency plasma induced grafting. JP-A-06/289332 discloses a contact lens the surface of which has a hydrophilic, hydrophobic microdomain structure. The hydrophilic property is obtained by surface hydrophilic treatment comprising plasma treatment wherein the convergence of the plasma particles is effected by forming a mask around the surface of the contact lens. JP-A-58/216222 discloses the production of contact lenses of excellent transparency and hydrophilicity by low temperature plasma treating silicon resin lenses and then low temperature plasma polymerizing of N-vinyl-pyrrolidone. Plasma polymerization of N-vinylpyrrolidone as a technique of wettable treatment on silicon rubber contact lenses is described by M. Kuriaki et al. in Kobunshi Ronbunshu (1985), pp. 841–847.

DD-A-277 466 and DD-A-298 268 disclose methods for immobilizing biologically active materials wherein a polymer layer is deposited on a solid carrier by plasma polymerization and the biologically active material is then adhered to the polymer layer. In this method a mask may be provided on the solid carrier having a freely selectable structure whereby the polymer is deposited only on the unmasked sides of the support.

While polymeric coatings prepared by in-glow plasma polymerization may have suitable hydrophilic surface properties they do not consist of chains with regular repeat units but tend to form an irregular three-dimensional crosslinked network; see A. P. Ameen et al., Polymer, vol. 35 (1994) p. 4382. These coatings do not possess a highly regular arrangement of unaltered monomer residues which is desirable in view of the permeability characteristics required in case of coatings for biomedical devices like contact lenses. A further problem encountered with the in-glow plasma polymerization process is that the deposition of the coating is usually accompanied by a simultaneous competitive surface erosion process caused by the bombardment by the highly activated molecule fragments. In-glow plasma polymerization thus proved to be unsuitable for preparing coatings on bio-medical substrates like contact lenses which satisfy all performance requirements, especially regarding permeability in case of extended wear lenses.

Modifications of the "in-glow" plasma polymerization process are "post-plasma" polymerization or -coating or -deposition which is also called "plasma-induced" polymerization or -coating or -deposition, and "after-glow" plasma-induced polymerization or -coating or -deposition which is also be called "downstream" plasma-induced polymerization or -coating or -deposition, or "remote" plasma-induced polymerization or -coating or -deposition.

For "post-plasma" polymerization the surface of a substrate is treated first with a non-polymerizable plasma gas (e.g. $H_2$, He or Ar) and then in a subsequent step the surface thus activated is exposed to a monomer with the plasma power having been switched off. The activation results in the plasma-induced formation of radicals on the surface which in the subsequent step initiate the polymerization of the monomer thereon.

Post-plasma polymerization for preparing contact lenses with good wettability is disclosed in JP-A-02/220024. In a three-step procedure plasma treatment of a contact lens substrate which comprises a methacrylate polymer is carried out followed by exposure to oxygen and then graft polymerization in aqueous solution. JP-A-62/010616 and JP-A-05/295144 disclose treatment of the surface of a contact lens by low-temperature plasma and then graft polymerizing a hydrophilic monomer onto the surface. DE-A-27 48 568 discloses a two-step procedure for the production of a hydrophilic silicon contact lens wherein the lens is subjected to low temperature gas plasma and then redox-graft polymerization to form a hydrophilic resin film on the treated surface is carried out. A three-step post plasma polymerization method is also disclosed in EP-A-574 352 wherein a polymer substrate is first placed in a plasma to form free radicals, then contacted with oxygen to form hydroperoxy groups on the surface and finally graft polymerization of an ethylenically unsaturated monomer and a crosslinker is carried out. Gas-plasma initiated polymerization of acrylate (s) in emulsifier containing aqueous medium and post polymerizing in the absence of plasma is disclosed in JP-A-59/025807. JP-A-04/067012 discloses plasma treatment to the surface of contact lenses and decoration of the lens surface using a polymeric material other than the lens material, wherein the plasma treatment is performed using diffuse plasma. The treatment is intended to impart hydrophilic properties to the surface for increasing wettability with a cornea. EP-A-220 919 discloses a contact lens comprising a triorganovinylsilane based polymer having on the surface a grafted hydrophilic polymer coating to impart eye compatibility and long term wearability. For production of the coating the lens surface may be subjected to low temperature gas plasma, then exposed to $O_2$ to form surface peroxide groups, then dipped in a solution of a monomeric diorgano divinyl silane followed by redox or thermal polymerization. WO-A-94/06485 discloses a contact lens with one or more wettable surfaces capable of holding a continuous layer of aqueous fluid thereon which comprises a carbohydrate covalently bound by a hydrolytically stable bond to a plasma surface prepared on the base material. The plasma surface prepared on a base material comprises either a plasma treated surface on a base material or a plasma polymer coated to a base material. JP-A-07/72430 discloses a contact lens having good water wettability and anti-fouling property wherein a monomer component containing a vinyl monomer having a phospholipid type structure is graft-polymerized on the surface of a contact lens base material which has been treated by active radiation, e.g. plasma to introduce peroxide bonds in the base material.

While post-plasma polymerization is a process in which the monomer to be polymerized is not exposed to the high energy plasma and is thus not suffering activation and/or fragmentation, the method is of limited use because of the low deposition rates.

In contrast to the above explained post-plasma polymerisation process in which polymerization is carried out on the activated substrate after the plasma power having been switched off "after-glow" plasma-induced polymerization is a process in which polymerization is effected in the presence of the plasma but wherein the substrate as well as the inlet for the monomer feed are located outside of (below) the plasma zone. Fragmentation of the monomer molecules can be largely avoided in this way as the monomer does not pass the zone of the highly reactive plasma gases. With this process the structure of the polymer deposit can be controlled within certain limits, undesired surface erosion of susceptible substrates can be avoided and the formation of the polymer deposit is predominantly based on radical reactions.

This modified plasma-induced polymerization process is described by B. D. Ratner in "Plasma Deposition of Organic Thin Films—Control of Film Chemistry" where it is stated that "placement of the sample downstream from the glow to allow it to receive reactive molecules from the gas phase that can condense and polymerize on its surface, but not subjecting it to bombardment by high energy species in the glow, has been shown, in a number of instances, to produce films with relatively intact chemistries." The author concludes, that "if conditions can be developed where significant conventional polymerization occurs along with the plasma deposition processes, much structure can be retained." A. Hartwick et al. report in Die Angewandte Makromolekulare Chemie 211 (1993), pp. 141–155 on after-glow plasma polymerization as a new method to prepare polymeric layers from unsaturated monomers. The authors give experimental parameters such as deposition rates, pressure, distance between plasma and deposition zone, flux and kind of auxiliary gas, stating that mostly the polymers prepared by after-glow plasma polymerization are cross-linked and therefore insoluble.

D. Yu and R. E. Marchant, Macromolecules, 22 (1989), p. 2957 and WO-A-92/02114 disclose the production of hydroxylated plasma-polymerized films for biomedical implants by plasma-polymerizing N-vinyl-2-pyrrolidone monomers and reducing the carbonyl groups in the resulting polymer to alcohol groups with an aqueous solution of sodium borohydride. This method is used for modifying the blood contact surface and for enhancing the compatibility of a biomedical device. DE-A-35 22 817 discloses the production of biocidal coatings by plasma after-glow polymerization or grafting of organo-metallic compounds. JP-A-57/205403 discloses a process for producing high molecular weight thin films by plasma polymerization wherein a high molecular monomer is introduced into the plasma of an inert gas which passes a mesh-type electrode and produces a high molecular thin film on a base plate which is outside both electrodes. The plasma polymerized film does not contain cross-linked bonds and is soluble to solvent. It is used e.g. as coating for optical lenses. WO-A-87/01040 discloses an improved intra-occular lens material which includes a polymer substrate which is preferably a poly (methylmethacrylate) modified by a gas plasma deposition of a fluorocarbon coating producing a rigid, low energy surface having significantly reduced cell damage with respect to corneal endothelial tissues. For coating the sample disks were placed downstream of the capacitance plates. Regarding endothelial damage the fluorocarbon coatings proved to be superior compared to HEMA, NVP or ethylene oxide coatings.

R. E. Marchant et al. report in Journal of Polymer Science Part A: Polymer Chemistry Vol. 27, 881–895 (1989) on the preparation and characterization of hydrophilic polymer films derived from the RF plasma polymerization of N-vinyl-2-pyrrolidone (NVP). In the plasma system used the monomer inlet extended 2 cm beyond the induction coil. Substrate samples were mounted on a glass-rod tray positioned at 5–30 cm from the coil. The structure of the deposited, plasma polymerized NVP (PPNVP) was determined i.a. by FT-IR-ATR spectroscopy and ESCA (Electron Spectroscopy for Chemical Analysis) and the spectra obtained were compared with the IR spectrum of linear PVP. The main differences observed were the broadening and loss of resolution in the 1600–1000 $cm^{-1}$ region of the PPNVP films, which contains the C-H deformation bonds, C-N stretching, and lactam ring skeletal modes. These differences between the plasma polymer and the PVP linear polymer analogue were attributed to branching, crosslinking, and ring opening reactions which occur to a larger extent in the high energy plasma environment.

The overview of the prior art documents relating to the after-glow embodiment of the plasma coating method shows that the reports on the products obtained with this relatively young technology are still contradictory. One of the documents states that the polymers prepared are cross-linked and therefore insoluble, while in another document they are described as not being cross-linked and soluble in solvents. While B. D. Ratner, loc. cit., speculates about the possibility to produce films with relatively intact chemistries, none of the other documents report about a high degree of retention of an intact polymer structure having desirable permeability characteristics. To the contrary, R. E. Marchant et al, loc cit., show that after-glow plasma polymerization of NVP under the reported conditions leads to branching, crosslinking and ring opening reactions giving a polymeric product which is largely different from linear PVP.

It is an object of the present invention to provide polymeric coatings having excellent adherence to the substrate by plasma-induced polymerization of polymerizable unsaturated compounds wherein the polymer chains while exhibiting controlled crosslinking are composed to a large extent of repeating units which are identical in structure to the repeating units obtained by non-plasma radical polymerization of the polymerizable unsaturated compound, which coating show outstanding thermal, oxidative and hydrolytic stability and resistance to delamination from the substrate caused by mechanical stress and desirable permeation characteristics for liquids, gases, ions and low molecular weight compounds while having controlled permeability for high molecular weight biocomponents, such as proteins, glycoproteins and lipids.

It is a further object of the present invention to provide coatings of the above mentioned type which may be applied to a wide variety of substrates including organic polymers and inorganic materials such as metals, ceramic materials, glass, minerals and carbon including graphite, or composites of these materials.

It is a more specific object of the invention to provide a coating on a biomedical material or article, especially a contact lens, most specifically an extended wear contact lens which coating is characterized by good adherence to the substrate and wear resistance, exhibits good permeability for oxygen, carbon dioxide, water and ions, high wettability, stability towards tear liquid and deposition of proteins, lipids, mucins and salts and shows excellent comfort for the wearer on continuous wearing of more than 6 days and 6 nights.

It is a further object of the invention to provide a method for preparing coatings having the above mentioned desirable properties in a simple and reliable one step process.

These objects could be achieved on the basis of the finding, that polymeric coatings having a variety of desirable characteristics as mentioned above can be produced by plasma-induced polymerization of a polymerizable unsaturated compound on a substrate in the after-glow zone of a plasma apparatus under specifically controlled conditions including the distance of substrate and monomer inlet to the plasma zone.

The subject matter of the present invention is thus an article comprising a substrate which is at least partially coated with a polymeric coating, said article being obtainable by after-glow plasma-induced polymerization of a polymerizable unsaturated compound on the substrate, wherein the substrate is positioned at a distance of 4 to 40 cm and the monomer inlet at a distance of 3 to 35 cm downstream outside the plasma zone, wherein the polymer chains of the coating are composed of 70% to 98% of repeating units which are identical in structure to the repeating units obtained by non-plasma radical polymerization of the polymerizable unsaturated compound and of 2% to 30% of repeating units which are sites of cross-linkage and/or covalent bonding to the substrate.

A further object is an article comprising a substrate which is at least partially coated with a polymeric coating, wherein the polymer chains of the coating are composed of 70% to 98% of repeating units which are identical in structure to those repeating units obtained by non-plasma radical polymerization of the polymerizable unsaturated compound (monomer) and of 2% to 30% of repeating units which are sites of cross-linkage and/or covalent bonding to the substrate.

The expressions "polymerizable unsaturated compound" and "monomer" are used hereinbefore and hereinafter synonymously.

According to the invention the adherence of the coating to the substrate and the degree of crosslinking of the polymeric coating are such that the coated article shows thermal, oxidative and hydrolytic stability and resistance to delamination caused by mechanical stress and that the coating is permeable to gases, water and ions having a molecular weight below 500 and has a controlled permeability for bio-components, such as proteins, glycoproteins and lipids.

In a specifically preferred aspect of the present invention the substrate which is at least partially coated with a polymer as indicated above is a biomedical material, article, or device including catheters and vascular grafts, especially an ophthalmic device for vision correction, such as a contact lens, an intraocular lens, or a lenticular corneal implant and most specifically an extended wear contact lens. The polymeric coating can also be in the form of a pattern.

According to a specific embodiment of the present invention the polymeric coating is a copolymer which is obtainable by after-glow plasma-induced polymerization as described above using a mixture of two or more polymerizable unsaturated compounds. In this embodiment copolymer-coatings of a well defined structure having predominantly repeating units identical in structure to those obtained by non-plasma radical copolymerization can be obtained.

According to another embodiment of the present invention the degree of crosslinking of the polymer or copolymer coating may be further controlled by adding at least one crosslinking agent to the monomer feed which is subjected to after-glow plasma-induced polymerization.

According to still a further embodiment of the present invention a laminate coating having "tailored" permeability and wettability performances as well as defined structure and morphology can be prepared by after-glow plasma-induced polymerization according to the present invention if two or more comonomers, optionally together with crosslinking agents are subjected to polymerization one after the other, preferably without interrupting the glow discharge.

A further subject matter of the present invention is a method for preparing an article as indicated above which comprises carrying out after-glow plasma-induced polymerization of a polymerizable unsaturated compound on a substrate wherein the substrate is positioned at a distance of 4 to 40 cm and the monomer inlet at a distance of 3 to 35 cm downstream outside the plasma zone.

After-glow plasma induced polymerization of a polymerizable unsaturated compound in accordance with the invention is preferably carried out under the following plasma conditions:

| | |
|---|---|
| Electric power | 40–300 watts |
| Electric voltage | $8 \cdot 10^2$–$4 \cdot 10^3$ volts |
| Plasma gas flow | 1–100 sccm (standard cubic centimeter) |
| Monomer flow | 1–50 mg/min |
| Feed gas flow | 1–100 sccm |
| Temperature of the monomer source | −80° C.–+80° C. |
| Frequency | 1 kHz–27.12 MHz, most preferably 13.6 or 27.12 MHz |
| Plasma gases | Ar, He, $N_2$ |
| Pressure | $1 \cdot 10^{-4}$–5 mbar, |

The substrate distance downstream from the plasma zone is preferably 8–30 cm, most preferably 10–25 cm. The monomer inlet distance downstream from the plasma zone is preferably 6–25 cm, most preferably 8–20 cm.

The polymeric coatings of the present invention which are obtainable by after-glow plasma-induced polymerization of a polymerizable unsaturated compound on a substrate under the afore-mentioned conditions regarding the distance between substrate and plasma zone as well as monomer inlet and plasma zone are characterized—contrary to coatings obtained by in-glow plasma-induced polymerization or by after-glow plasma-induced polymerization without observing these conditions—by the fact that the repeating units of the polymer chains are to a large extent identical in structure to those repeating units obtained through a non-plasma radical polymerization of the respective unsaturated compound. From 70% to 98%, preferably from 76% to 98%, more preferably from 82% to 98% of the repeating structural units exhibit the same structure as the polymer obtained by non-plasma radical polymerization of the same monomer. The remaining 2% to 30%, preferably 2% to 24%, more preferably 2% to 18% of the structural units serve as covalent linking groups to the coated substrate or as crosslinking sites between adjacent polymer chains.

The qualitative and quantitative characterization of a plasma-induced polymer coating of the present invention may typically be determined as outlined below.

Three coatings, each based upon N-vinyl pyrrolidone are prepared. The first coating (1) is a solvent cast film of poly-vinylpyrrolidone (PVP) made by radical polymerization; the second coating (2) is a PVP-film prepared in accordance to the present invention; and the third coating (3) is a so called "in glow" plasma-polymerized PVP-film (see introductory portion of present invention). The above three films are investigated by Fourier Transformation Infrared—Attenuated Total Reflection Spectroscopy (FTIR-ATR, see also working examples). The first (1) and second (2) coating exhibit essentially identical IR-spectra, whereas the third (3) coating shows a distinctly different IR-spectrum. Based upon the approximately 5% detection limit of the FTIR-ATR investigation method, it can be concluded that the coatings (1) and (2) are basically identical in their chemical structure.

The uniform structure and the controllable relatively low degree of crosslinking of the coatings which is surprisingly achieved in the after-glow or downstream embodiment of the plasma-induced polymerization of a polymerizable unsaturated compound under the specific conditions of the position of substrate and monomer inlet constitutes a characteristic feature of the coatings which is responsible for a wide variety of advantageous properties exhibited by these coatings, especially in view of their use in biological systems including biomedical applications, articles or devices.

A specific advantage of the coatings is their strong adherence to the surface of the coated substrate which is obtained to a large degree independently from the nature of the substrate, whether it is a polymeric organic material or an inorganic material such as a metal, ceramic material, glass or a mineral or carbon, especially graphite or glassy carbon. Also composite materials including two or more of the above mentioned substrate materials may be coated with the coating of the invention.

The high degree of structural uniformity of the polymer chains of the coating of the invention and the low degree of crosslinking as well as the excellent adherence of the coatings to the substrate provide the coatings of the invention with superior characteristics for a wide variety of applications including:

excellent adherence to the substrate and wear resistance;
excellent thermal oxidative and hydrolytic stability and resistance to delamination caused by mechanical stress;
good permeation characteristics for liquids, gases, ions and low molecular weight compounds;
controlled permeability for biocomponents, such as proteins, glycoproteins and lipids;
high resistance against temperature changes, autoclaving, bioerosion, swelling and shear forces;
smooth surface down to the sub-micron area, uniform sheet thickness and excellent lubrication properties;
high resistance and durability in biological surroundings, good resistance against formation of irreversible deposits of components from biological systems, such as proteins, lipids, glycoproteins, salts and metabolites and cell debris;
low tendency for absorption of substances from the surroundings, such as cosmetics, solvent vapors and dusts;
substantially no tendency for adherence of microorganisms.

The extraordinary features of the coatings with regard to adhesivity and permeability are due to the fact that polymer chains within the coating still possess pronounced dynamics and mobility.

There is essentially no limitation with respect to the form of the substrate to be coated for preparation of an article according to the invention, as long as it can be brought into and held in the after-glow zone of a plasma generating device. Specific examples of forms of substrates which may be coated according to the invention include films, fibers, membranes, sheets, hoses, tubes, hollow fibers, capsules, beads and granules of different size including powder type materials as well as composites and laminates. A specific group of substrates which is envisaged within this invention are biomedical materials or articles, especially ophthalmic devices for vision correction. These include contact lenses, intraocular lenses and lenticular corneal implants (artificial cornea).

The substrate includes any material conventionally used for the manufacture of biomedical devices, e.g. contact lenses, which are not sufficiently hydrophilic per se. Such materials are known to the person skilled in the art and may comprise for example polysiloxanes, fluorinated (meth) acrylates or equivalent fluorinated comonomers derived e.g. from other polymerizable carboxylic acids, alkyl (meth) acrylates or equivalent alkyl comonomers derived from other polymerizable carboxylic acids, or fluorinated polyolefins, such as fluorinated ethylene or propylene polymers and copolymers, or tetrafluoroethylene, preferably in combination with specific dioxols, such as perfluoro-2,2-dimethyl-1,3-dioxol. Examples of suitable substrate materials are e.g. Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

The substrate also includes any material conventionally used for the manufacture of biomedical devices, e.g. contact lenses, which are hydrophilic per se, since reactive groups, e.g. amine or hydroxy groups are inherently present in the material and therefore also at the surface of a biomedical device manufactured therefrom. Such materials are known to the person skilled in the art. Typical examples comprise e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon or Atlafilcon. Most of these materials are HEMA based, but suitable materials may also be based on other underlying monomers or polymers having reactive groups, e.g. hydroxy groups or amino groups, such as e.g. polyvinyl alcohol.

The substrate may by any blood-contacting material conventionally used for the manufacture of renal dialysis membranes, blood storage bags, pacemaker leads or vascular grafts. For example, the substrate may be a polyurethane, polydimethylsiloxane, polytetrafluoroethylene, perfluoroalkyl-polyether, polyvinylchloride or Dacron™.

In a specifically preferred embodiment of the present invention the substrate to be coated is a contact lens suitable for extended wear, i.e. for continuous wear of more than six days and six nights up to a time of about 30 days. This type of soft contact lenses includes those comprising polysiloxane and/or perfluoroalkyl-polyether groups which exhibit the desired high oxygen- as well as high ion- and water-permeability. If this type of substrate is coated in accordance with the present invention with a hydrophilic monomer, coated contact lenses are obtained which exhibit the following desirable properties as compared to conventionally surface coated contact lenses:

increased permeability for oxygen, carbon dioxide, water and ions;
excellent wettability, lubricity and stability in the ocular liquid surroundings;
improved comfort for the wearer as well as resistance against irreversible deposition of substances occurring in the ocular surroundings, including proteins, lipids, mucins and salts;
decreased adhesiveness for microorganisms;
decreased tendency of microcrack formation within the coating during sterilization in the autoclave in phosphate buffered saline;
superior on-eye performance including very low cornea swelling, eye irritation and very good mobility on the eye during continuous wear of the lens over an extended time of up to 30 days.

In the case of implants a coating in accordance with the present invention prepared from a hydrophilic monomer provides articles having surface characteristics including an open, only slightly cross-linked polymer structure which exhibits excellent biocompatibility and leads to good and durable integration into the living tissue.

The monomer which may be used to prepare the polymeric coatings by after-glow plasma-induced polymerization may be any polymerizable unsaturated compound which can be evaporated and introduced into the after-glow zone of a plasma generating apparatus to contact the substrate provided therein. Preferred monomers are vinyl compounds such as (meth)acrylic derivatives, vinyl ethers, N-vinyl pyrrolidone and vinyl pyridine.

Specific examples of preferred acrylic derivatives include acrylic acid, methacrylic acid, hydroxyethyimethacrylate (HEMA), methylmethacrylate (MMA), dimethylaminoethyl-methacrylate (DMAEMA), 2-hydroxyethylacrylate (HEA), N,N-dimethylacrylamide (DMA), N-acryloylmorpholine (NAM) and ethylene glycol dimethacrylate (EDGMA).

N-vinylpyrrolidone is an especially preferred monomer for preparing the polymeric coatings according to the invention.

Specific examples of suitable vinyl ethers are methylvinyl ethers, ethylvinyl ether and methoxyethylvinyl ether.

The above monomers, the vinyl compounds, might be used individually or in mixtures.

The polymeric coatings are prepared on at least a part of the surface of a substrate to give a coated article of the invention by plasma-induced polymerization of a polymerizable unsaturated compound in the after-glow or downstream area of a plasma reactor. The process parameter including the physical plasma parameters are controlled for the deposition process in such a way that the desired amount of repeating units which are identical in structure to those repeating units obtained by non-plasma radical polymerization of the polymerizable unsaturated compound, the desired degree of crosslinking and the desired morphology and topography are obtained on the specific substrate. These parameters and characteristics as well as the thickness of the coating may be tailored within broad ranges by suitably selecting the plasma and reaction parameters. Compared to other coating processes the method according to the invention offers the following advantages (e.g. for coating contact lenses):

it is carried out as a one step process;

the coated substrates are obtained under sterile conditions;

very low surface erosion and high deposition rate;

smooth, pinhole-free coatings are obtained;

the thickness of the coating can easily be controlled up to relatively thick coatings of more than 1 $\mu$m;

low content of radicals remaining in the coating;

no secondary reactions with air to hydroperoxides and other reactive species;

excellent thermal and hydrolytic stability of the coatings which do not contain leachable parts;

high UV and light stability of the coatings;

uniform layer thickness on non-flat substrates including good edge coating;

homogenous surface groups;

high content of "brush-type" surface structures with low tendency for denaturization of biopolymers or other biocomponents and irreversible adsorption (biofouling);

no fragmentation of the monomers employed and no bombardment of the surface of the substrate by atoms, ions, excited species or high energy UV-radiation during the coating process leading to undesired secondary changes of the coating and/or the substrate and to detrimental surface erosion.

no tendency to delamination of the coatings on thermal, hydrothermal and mechanical stress.

As already mentioned above, in an important aspect, the present invention refers to contact lenses comprising the polymeric coating according to the invention on a suitable lens body which—based upon the outstanding properties of the coating including high oxygen transmissibility, good movement on the eye and high permeability for ions and water—may be used for extended periods of wear, e.g., up to 30 days. Important characteristics of such contact lenses and methods for their determination will be explained in the following:

Oxygen Transmissibility and Permeability.

The "oxygen transmissibility" of a lens, as used herein, is the rate at which oxygen will pass through a specific ophthalmic lens. Oxygen transmissibility, $D_k/t$, is conventionally expressed in units of barrers/mm, where t is the average thickness of the material [in units of mm] over the area being measured and "barrer" is defined as:

$$[(cm^3\ oxygen)(mm)/(cm^2)(sec)(mm\ Hg)] \cdot 10^{-9}$$

The "oxygen permeability", $D_k$, of a lens material does not depend on lens thickness. Oxygen permeability is the rate at which oxygen will pass through a material. Oxygen permeability is conventionally expressed in units of barrers, where "barrer" is defined as:

$$[(cm^3\ oxygen)(mm)/(cm^2)(sec)(mm\ Hg)] \cdot 10^{-10}$$

These are the units commonly used in the art. Thus, in order to be consistent with the use in the art, the unit "barrer" will have the meanings as defined above. For example, a lens having a $D_k$ of 90 barrers ("oxygen permeability barrer") and a thickness of 90 microns (0.090 mm) would have a Dk/t of 100 barrers/mm("oxygen transmissibility barrers"/mm).

The oxygen transmissibility of the extended-wear lens from the outer surface to the inner surface must be sufficient to prevent any substantial corneal swelling during the period of extended wear. It is known that the cornea swells approximately 3% to 4% during overnight periods of sleep when the eyelids are closed, as a result of oxygen deprivation. It is also known that wearing a conventional contact lens for a period of about 8 hours (overnight wear) causes corneal swelling of about 11%. However, an acceptable extended-wear contact lens will produce, after wear of about 24 hours, including normal sleep periods, corneal swelling of less than about 8%, more preferably less than about 6%, and most preferably less than about 4%. A preferred extended-wear contact lens will produce, after wear of about 7 days, including normal sleep periods, corneal swelling of less than about 10%, more preferably, less than about 7%, and most preferably less than about 5%. Thus, the extended-wear lens must have oxygen permeable polymer in an amount sufficient to produce oxygen diffusion to yield the above properties relating to corneal swelling. Preferably, the extended-wear lens has a continuous phase of oxygen permeable polymer extending from the outer surface to the inner surface of the lens.

The oxygen permeability of a lens and oxygen transmissibility of a lens material may be determined by the following technique. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm³/min., while a nitrogen stream is passed on the opposite side of the lens at a rate of about 10 to 20 cm³/min. The barometric pressure surrounding the system, $P_{measured}$, is measured. The thickness (t) of the lens in the area being exposed for testing is determined by measuring about 10 location with a Mitotoya micrometer VL-50, or similar instrument, and averaging the measurements. The oxygen concentration in the nitrogen stream (i.e., oxygen which diffuses through the lens) is measured using the DK1000 instrument. The oxygen permeability of the lens material, $D_k$, is determined from the following formula:

$$D_k = Jt(P_{oxygen})$$

where

J=oxygen flux [microliters $_{O2}$/cm²–minute]

$P_{oxygen}=(P_{measured}-P_{water\ vapor})\cdot(\%O_2$ in air stream)[mm Hg]=partial pressure of oxygen in the air stream $P_{measured}$=barometric pressure [mm Hg]

$P_{water\ vapor}$=0 mm Hg at 34° C. (in a dry cell) [mm Hg]

$P_{water\ vapor}$=40 mm Hg at 34° C. (in a wet cell) [mm Hg]

t=average thickness of the lens over the exposed test area [mm]

where $D_k$ is expressed in units of barrers, i.e., [(cc oxygen)(mm)/cm²]·[sec/mm Hg]·$10^{-10}$.

The oxygen transmissibility ($D_k/t$) of the material may be calculated by dividing the oxygen permeability ($D_k$) by the average thickness (t) of the lens.

The oxygen transmissibility ($D_k/t$) of the extended-wear lens of the invention is preferably at least 70 barrers/mm, more preferably at least 75 barrers/mm, and most preferably at least 87 barrers/mm. The lens center thickness is typically more than about 30 microns, preferably about 30 to about 200 microns, more preferably about 40 to about 150 microns, even more preferably about 50 to about 120 microns, and most preferably about 60 to 100 microns.

Ionoflux Measurement Technique

The following technique, referred to herein as the "ionoflux Technique", is a preferred method for determining the ion permeability of a lens. This technique may be used to determine the likelihood of adequate on-eye movement.

The "Ionoflux Technique" involves the use of a conductometer (LF 2000/C, catalog, no. 300105, Wissenschaftlich-Technische Werkstätten GmbH (WTW), Germany), an electrode equipped with a temperature sensor (LR 01/T, catalog no. 302 520, (WTW)), a donor chamber containing a salt solution, a receiving chamber containing about 60 ml of deionized water, a stir bar and a thermostat.

The donor chamber is specially designed for sealing a contact lens thereto, so that the donor solution does not pass around the lens (i.e., ions may only pass through the lens). The donor chamber is composed o f a glass tube which is threaded at the end which is immersed in the receiving solution. The glass tube includes a centrally located hole of about 9 mm in diameter. A lid, which is threaded to mate with the glass tube, holds a lens-retaining member which includes a centrally located hole of about 8 mm in diameter. The lens-retaining member includes a male portion adapted to mate with and seal the edges of the inner (concave) surface of a lens and a female portion adapted to mate with and seal the edges of the outer (convex) surface of a lens.

The lens to be measured is placed in the lens-retaining member, between the male and female portions. The male and female portions include flexible sealing rings which are positioned between the lens and the respective male or female portion. After positioning the lens in the lensretaining member, the lens-retaining member is placed in the threaded lid. The lid is screwed onto the glass tube to define the donor chamber. The donor chamber is filled with 16 ml of 0.1 molar NaCl solution. The receiving chamber is filled with 60 ml of deionized water. The leads of the conductivity meter are immersed in the deionized water of the receiving chamber and a stir bar is added to the receiving chamber. The receiving chamber is placed in a thermostat and the temperature is held at about 35° C. Finally, the donor chamber is immersed in the receiving chamber.

Measurements of conductivity are taken every 20 minutes for about three hours, starting 10 minutes after immersion of the donor chamber into the receiving chamber. The Ionoflux Diffusion Coefficient, D, is determined by applying Fick's law as follows:

$$D = -n'/(A \cdot dc/dx)$$

where n'=rate of ion transport [mol/min]

A=area of lens exposed [mm²]

D=Ionoflux Diffusion Coefficient [mm²/min]

dc=concentration difference [mol/L]

dx=thickness of lens [mm]

An Ionoflux Diffusion Coefficient of greater than about $6.4 \cdot 10^{-6}$ mm²/min is preferred for achieving sufficient on-eye movement. More preferably, the Ionoflux Diffusion Coefficient is greater than about $2.6 \cdot 10^{-6}$ mm²/min, while most preferably the Ionoflux Diffusion Coefficient is greater than about $1.5 \cdot 10^{-5}$ mm²/min. It must be emphasized that the Ionoflux Diffusion Coefficient correlates with ion permeability through the lens, and thereby is a predictor of on-eye movement.

Contact Angle Measurements

Advancing and receding water contact angles of coated and non-coated lenses were determined with the dynamic Wilhelmy method using a Krüss K12 instrument (Krüss GmbH, Hamburg). For details it is referred to D. A. Brandreth: "Dynamic contact angles and contact angle hysteresis", Journal of Colloid and Interface Science, vol. 62, 1977, pp. 205–212 and R. Knapikowski, M. Kudra: Kontaktwinkelmessungen nach dem Wilhelmy-Prinzip—Ein statistischer Ansatz zur Fehlerbeurteilung", Chem. Technik, vol. 45, 1993, pp. 179–185. The following parameters are usually determined infra: The advancing angle (Adv.), the receding angle (Rec.) and the Hysteresis. The coating having polysiloxane and/or perfluoroalkyl groups may exhibit a wettability, expressed as the contact angle with water of $\leq 75°$ advancing, $<65°$ receding and $<46°$ hysteresis.

Determination of the Percentage of Repeating Units in the Polymeric Coating Having Identical Structure as Non-Plasma Radically Polymerized Polymer Quantification is accomplished by Fourier Transformation Infrared—Attenuated Total Reflection (FTIR-ATR) Spectroscopy. A Bruker IFS-55 FTIR Spectrometer equipped with a liquid nitrogen cooled medium-bandpass mercury-cadmium-telluride (MCT) detector is used. A germanium trapezoide crystal with a dimension of 32·20·3 mm and an end-face angle of 45° obtainable from Graseby Specac NIC is employed as an internal reflection element (IRE). 500 scans are coded at a resolution of 4 cm$^{-1}$ for the spectrum. A solvent-cast film (0.005 mm thickness) of poly-vinylpyrrolidone (PVP) made by radical polymerization and a PVP coated contact lens (PVP-CL) prepared according to the plasma-induced after glow procedure given above are investigated by the above setup. In order to achieve optimum contact the samples are tightly pressed onto the germanium crystal surface for ATR measurements. The lens is positioned on the crystal with the coated surface downwards. Absorption bands at wavenumbers 1668, 1494, 1461, 1424, 1375 and 1287 in the PVP spectrum and absorption bands at 1671, 1494,1462, 1375 and 1287 $cm^{-1}$ in the PVP-CL spectrum are selected for the comparison. From calculations based on the relative intensities of the absorptions result a content of the polymer coating of 90%±8% of repeating units of the structure:

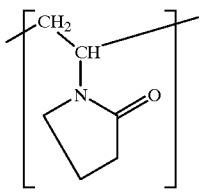

The thickness of a polymeric coating according to the invention is typically in the range of 1–5000 nm, preferably in the range of 5–1000 nm, more preferably in the range of 15–350 nm and in particular in the range of 30–150 nm.

EXAMPLES

The present invention is further explained with reference to specific embodiments in the following examples which are directed to contact lenses coated with a polymeric coating according to the invention. They should not be construed to limit the scope of the claims. All temperatures are given in degrees Celsius.

I. Preparation of Contact Lenses as Substrates
Example A-1
Macromer Synthesis A polysiloxane macromer is prepared by reacting, at room temperature (about 21° C.), one mole equivalent (about 100 g) of poly(dimethylsiloxane) dialkanol (Shin Etsu Chemical Co., Tokyo, Japan) having hydroxyethyl propoxy end groups with 2 mole equivalents (about 21.2 g) of isophorone diisocyanate (Aldrich Chemical Co., Milwaukee, Wis. USA) in the presence of about 0.2 g dibutyltin dilaurate catalyst (Pfaltz & Bauer, Inc., Waterbury, Conn. USA). After about 48 hours reaction time, 2.02 mole equivalents (about 38.7 g) of poly(ethylene glycol) ("PEG", number-average molecular weight (Mn) about 610, Dow Chemical Corp., Midland, Minn. USA) and about 0.17 g of dibutyltin dilaureate (about 0.43% by weight based on PEG) are added to 80 g of the reaction product from the prior step. Sufficient chloroform (Aldrich Chemical Co.) is added to make the mixture homogeneous. This mixture is stirred at room temperature for about 15 hours. Next, the mixture is stirred for about 8 hours at a temperature of about 44 to 48° C., with the temperature held substantially constant by a surrounding oil bath. The chloroform is then evaporated, in order to achieve a final concentration of about 50% by weight solids, by stirring the mixture at room temperature for about 8 hours. Then, about 2.14 mole equivalents (about 10.4 g) of isocyanatoethyl methacrylate ("IEM", Monomer Polymer, Inc., Feasterville, Pa. USA) is added to the mixture. Finally, the mixture is covered with aluminum foil and stirred at room temperature for about 17 hours, yielding a polysiloxane-containing macromer having a Mn of about 4,000.

Example A-2
Production of a Contact Lens

A polysiloxane macromer is first prepared substantially in accordance with the procedure described in Example A-1.

A copolymer precursor solution is prepared by mixing about 180 g polysiloxane-containing macromer, about 15 g 3-methacryloxypropyltris (trimethylsiloxy) silane (Shin Etsu), about 4 g 2-hydroxyethyl methacrylate ("HEMA"), about 1 g ethylene glycol dimethacrylate ("EGDMA"), and about 1 g DAROCUR® 1173 photoinitiator at room temperature for about 16 hours.

The copolymer precursor solution is then polymerized to form contact lenses. Polypropylene contact lens molds are filled with the copolymer precursor solution. Ultraviolet light (about 300 to 400 nm) at about 3–6 $mW/cm^2$ is applied to the solution in the mold for about 3 hours at room temperature. The UV light causes polymerization, thereby allowing the solution to form a contact lens having the shape of the mold. The lens is extracted with isopropanol to remove remaining chloroform solvent and any unreacted components. A preferred resulting polymer contains about 81.8% by weight of polysiloxane macromer, about 13.6% TRIS, about 3.6% 2-hydroxyethyl methacrylate, and about 0.9% EGDMA. The contact lens is degassed by placing the lens under suitable vacuum for a period sufficient to remove substantially all gas from the lens matrix. Fully hydrated degassed contact lenses having this composition exhibit a $D_k$ of about 87 barrer, a water content of about 19% by weight and a modulus of elasticity of about 2.5 MPa. Ionoflux ion permeability coefficient is determined to be about $3.14 \cdot 10^{-5}$ $mm^2/min$.

Example A-3
Macromer Synthesis 51.5 g (50 mmol) of the perfluoropolyether Fomblin® ZDOL (from Ausimont S.p.A., Milan, Italy) having a mean molecular weight of 1,030 g/mol and containing 1.96 meq/g of hydroxyl groups according to end-group titration is introduced into a three-neck flask together with 50 mg of dibutyltin dilaureate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the α,ω-hydroxypropyl-terminated polydimethylsiloxane KF-6001 from Shin Etsu having a mean molecular weight of 2,000 g/mol (1.00 meq/g of hydroxyl groups according to titration) are introduced into a flask. The flask contents are evacuated to approximately 0.1 mbar and decompressed with argon. This operation is repeated twice. The degassed siloxane is dissolved in 202 ml of freshly distilled toluene kept under argon and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g). 13.78 g (88.9 mmol) of 2-isocyanatoethyl methacrylate (IEM) are added under argon to 247 g of the α,ω-hydroxypropyl-terminated polysiloxane-perfluoropolyether-polysioxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colorless and clear. It can be stored in air at room temperature for several months in the absence of light without any change in molecular weight.

Example A-4
Production of a Contact Lens 13.0 g of macromer from Example A-3 are dissolved in 5.6 g of ethanol (Fluka, puriss. p.a.) (70% by weight solution). After complete homogenization of the solution, 5.2 g of 3-tris-(trimethylsilyloxy)silylpropyl methacrylate (TRIS from Shin Etsu, product no. KF-2801), 7.8 g of freshly distilled N,N-dimethacrylamide (DMA) and 160 mg of photoinitiator DAROCUR® 1173 (Ciba) are added. This solution is filtered through a Teflon membrane having a pore width of 0.45 mm under an argon pressure of from about 1 to 2 bar. The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert gas atmosphere, where the solution is pipetted into dust-free contact lens molds made from polypropylene. The molds are closed, and the polymerization reaction is effected by UV irradiation (15 mW/cm$^2$, 5 min.), with simultaneous crosslinking. The molds are then opened and placed in ethanol, causing the resulting lenses to swell out of the molds. The lenses are extracted for 24 hours with constantly replenished distilled dichloromethane and subsequently dried in a high vacuum. The dried lenses are equilibrated in phosphate-buffered physiological saline solution in autoclave-resistant vials and then autoclaved at 120° C. for 30 minutes. All physical data measurements are carried out on autoclaved lenses.

The lenses produced in this way are characterized by the following data: Oxygen permeability ($D_k$): 77 barrer (determined by the "wet" method described below), water content of the equilibrated lenses: 32% by weight, elongation at break at 35° C.: 360%, modulus of elasticity at 30° C.: 0.5 MPa (measured using a Minimat from Polymer Laboratories, UK). Ionoflux ion permeability coefficient is determined to be 71.0·10$^{-6}$ mm$^2$/min.
Production of a Contact Lens Example A-5

The process described under Example A-4 for the production of contact lenses is repeated, except that a mixture of comonomers having the following composition (in percent by weight) is used:

| 55% | macromer of Example B-1 |
| --- | --- |
| 22% | TRIS |
| 22.5% | DMA |
| 0.5% | 2-hydroxy-3-methacryloxypropyl trimethylammonium chloride (Blemer ®QA) |

The lenses produced are characterized by the following data. Ionoflux ion permeability coefficient: 8.5·10$^{-6}$ mm$^2$/min, O$_2$D$_k$: 106 barrer, water content: 23%.

Example A-6
Production of a Contact Lens

Lenses are prepared in accordance with the procedures described in Example A-4, except that a mixture of comonomers having the following composition (in percent by weight) is used:

| 60% | macromer of Example A-3 |
| --- | --- |
| 25% | TRIS |
| 15% | DMA |

The lenses produced are characterized by the following data. Ionoflux ion permeability coefficient: 1.5·10–6 mm$^2$/min, O$_2$D$_k$: 130 barrer, water content: 7%.

Example A-7
Macromer Synthesis

Reaction of α,ω-bis-aminopropyl-dimethylpolysiloxane with D(+)gluconic acid δ-lactone:

The amino-functionalized polydimethylsiloxane to be employed for the synthesis (X-22-161-C, Shin Etsu) is first finely dispersed in acetonitrile, extracted and then subjected to molecular distillation.

The following reactions take place with the exclusion of H$_2$O. 200 g of purified amino-functionalized polydimethylsiloxane (0.375 meq of NH$_2$/g; Mn (VPO) 3400–3900 (VPO=Vapour Pressure Osmometry)), dissolved in 200 ml of absolute THF, are added dropwise to a suspension of 13.35 g (75 mmol) of D(+)gluconic acid δ-lactone in 50 ml of absolute THF and the mixture is stirred at 40° C. for about 24 hours until the lactone has reacted completely. The reaction is monitored by thin layer chromatography (TLC): silica gel; i-propanol/H$_2$O/ethyl acetate 6:3:1, staining with Ce(IV) sulfate/phosphoromolybdic acid solution (CPS reagent). After completion of the reaction, the solution is concentrated to dryness and the residue is dried under 3 Pa (0.03 mbar) for 48 hours. 213.3 g of α,ω-bis (3-gluconamidopropyl)-poly-dimethylsiloxane were obtained. Titration of the amino groups with perchloric acid show more than 99.8% conversion of the amino groups.

Reaction of α,ω-bis-3-gluconamidopropyl-dimethylpolysiloxane with IEM: The product obtained above (213.3 g) is dissolved in 800 ml of absolute THF and the solution is heated to 40° C. with the addition of catalytic amounts of dibutyltin dilaurate (DBTDL). 14 g (90 mmol) of IEM in 20 ml of absolute THF are added dropwise to this solution over a period of about 4 hours. This corresponds to a concentration of 1.2 equivalents of IEM per gluconamide unit. The reaction is carried out in the course of 48 hours while monitoring the presence of NCO bonds by IR spectroscopy. The reaction solution is concentrated and the product dried in a brown glass flask under 3 Pa (0.03 mbar) for 24 hours, while cooling with ice. Yield: 227.2 g of a colorless rubber elastic product of high optical transparency.

Example A-8
Production of a Contact Lens

Before polymerization, the acrylates employed, N,N-dimethylacrylamide (DMA) and (3-methacryloyloxypropyl)-tris(trimethylsilyloxy)silane (TRIS) are freed from inhibitors by distillation. 0.80 g (8.1 mmol) of DMA and 0.804 g (1.9 mmol) of TRIS are weighed into a 50 ml round bottom flask and the flask is flushed with N$_2$ for half an hour, while cooling with ice. 0.80 g of macromer from Example A-7 are transferred to a round bottom flask under nitrogen, degassed under 3 Pa (0.03 mbar) for 24 hours and then dissolved in 2.7 g of ethanol which has been flushed with $N_2$ for half an hour beforehand. The subsequent preparation of samples and the polymerization are carried out inside a glove box in the absence of oxygen. The above monomer mixture and the macromer solution from Example A-7 are mixed, with the addition of 0.012 g (0.21 mmol) of DAROCUR® 1173 and the mixture is subjected to microfiltration (0.45 mm filter). 180 μl of this mixture are introduced into a polypropylene mold, which is then closed with an appropriate lid of polypropylene. The mixture is then irradiated with a UV-A mercury high pressure lamp in a nitrogen atmosphere in an accordingly equipped UV oven for 5 minutes. The lamps (5 each of the brand TLK40W/10R, Philips) are located above and below the holder inserted. The irradiation intensity is 14.5 mW/cm$^2$.

The polypropylene mold is opened and the finished discs or lenses are removed by soaking with a solvent mixture of methylene chloride and ethanol (2:3). The lenses and discs are extracted in ethanol at room temperature in special polypropylene cages for 48 hours and then dried at 40° C. under 10 Pa (0.1 mbar) for 24 hours (autoclaving at 120° C., 30 minutes). The discs exhibit an E modulus of 0.7 MPa, a permeability to oxygen of 96 barrer, a hardness (Shore A) of 53, and a Ionoflux of $27.0 \cdot 10^{-6}$ mm$^2$/min.

II. Generation of Plasma Grafted Coatings

Example B-1

Plasma-induced Polymerization of N-vinyl-2-pyrrolidone (Poly-NVP Coating Type 1)

The substrates including two lenses from Example A-2, two lenses from Example A-4, two lenses from Example A-5 and two lenses from Example A-8 are, after extraction in isopropanol and drying, placed on a glass holder within the plasma reactor. The distance between the substrates and the lower edge of the plasma zone is 25 cm. The reactor is evacuated to a pressure of 0.010 mbar, and held at these conditions for one hour. Then, the argon gas flow rate into the plasma zone of the reactor is set to 40 sccm, the pressure in the reactor adjusted to 0.3 mbar and the RF generator (27.12 MHz radio frequency generator, HFA Koppold & Co., Hohenkirchen, Germany) switched on. A plasma discharge having a power of 100 Watts is maintained for a total period of 1 minute. Thereafter, the following parameters for plasma-induced polymerization of NVP are maintained: Argon flow rate for plasma excitation: 30 sccm, argon carrier gas flow rate for monomer (NVP) transport: 50 sccm, temperature of the monomer (NVP) evaporation unit: 45° C., pressure: 0.35 mbar, and plasma power: 60 W. After 10 minutes of deposition, the plasma discharge is interrupted, the reactor evacuated and maintained for 30 minutes at a pressure of 0.010 mbar. The internal pressure is then brought to atmospheric pressure using dry nitrogen.

The substrates are then turned over and the whole procedure is repeated to coat the other side of the substrates.

The samples are then unloaded from the reactor, extracted in HPLC-water and analyzed by AFM, ATR-FTIR and contact angle measurement. The thickness of the coatings is in the range of 160–200 nm as determined by ellipsometry on analogous coatings, which have been deposited on silicon wafers.

Analysis of the modified substrates:

| Substrate from Example: | A-2 | A-4 | A-5 | A-8 |
|---|---|---|---|---|
| Contact angle [°] Adv./Rec./Hysteresis | 75/65/10 | 64/53/11 | 51/41/10 | 60/41/19 |
| Ionoflux [mm$^2$/min] | $2.7 \cdot 10^{-5}$ | $6.6 \cdot 10^{-5}$ | $7.5 \cdot 10^{-6}$ | $3.1 \cdot 10^{-5}$ |
| O$_2$D$_k$ [barrer] | 80 | 71 | 96 | 85 |
| On-eye movement | Yes | Yes | Yes | Yes |

Example B-2

Plasma-induced Polymerization of N-vinyl-2-pyrrolidone (Pol-NVP Coating Type 2)

Similarily to Example B-1 the substrates including two lenses from Example A-2, two lenses from Example A-4 and two lenses from Example A-8 are, after extraction in isopropanol and drying, placed on the glass holder which was positioned in the reactor at a distance of 20 cm from the lower edge of the plasma zone. After the samples have been mounted, the pressure in the system is lowered to 0.010 mbar, and held at these conditions for one hour. Then, the argon plasma gas flow rate into the plasma zone of the reactor is set to 40 sccm, the pressure in the reactor adjusted to 0.2 mbar and the RF generator switched on. Plasma discharge of a power of 100 Watts is maintained for a total period of 1 minute. After this pretreatment period, the following parameters for the plasma-induced grafting of NVP are established: Argon flow rate for plasma excitation: 20 sccm, argon carrier gas flow rate for monomer (NVP) transport: 25 sccm, temperature of the monomer (NVP) evaporation unit: 40° C., pressure: 0.30 mbar, and distance between the lower edge of the plasma zone and the substrates: 15 cm. The graft polymerization is performed at a plasma power of 100 W for 7.5 minutes. At the end of the reaction period, the base pressure of 0.010 mbar is restored and maintained for 30 minutes. The base pressure is then brought to atmospheric pressure using dry nitrogen.

The substrates are then turned over and the whole procedure is repeated to coat the other side of the substrates.

The samples are then unloaded from the reactor, extracted in HPLC-water and analyzed by AFM, ATR-FTIR and contact angle measurement.

Determination of the coating thickness by Atomic Force Microscopy (AFM):

According to the procedure outlined above a contact lens is coated with PVP. Before exposition to the plasma treatment process half of the lens has been tightly covered with a thin Teflon film, in order to prevent polymer deposition on this part of the lens. After removal of the Teflon shielding and autoclaving at 121° C./30 minutes in phosphate buffered saline at pH 7.4 the surface of the hydrated lens is investigated by AFM in the tapping mode. The step between the coated and the uncoated area of the lens surface can thus clearly be identified. The height of the step which corresponds to the coating thickness is found to be in the range of 60–70 nm.

Analysis of the modified substrates:

| Substrate from Example: | A-2 | A-4 | A-8 |
|---|---|---|---|
| Contact angle [°] Adv./Rec./Hysteresis | 69/49/20 | 66/47/19 | 68/34/31 |

-continued

Analysis of the modified substrates:

| Substrate from Example: | A-2 | A-4 | A-8 |
|---|---|---|---|
| Ionoflux [mm$^2$/min] | $2.9 \cdot 10^{-5}$ | $6.8 \cdot 10^{-5}$ | $2.8 \cdot 10^{-5}$ |
| O$_2$D$_k$ [barrer] | 78 | 68 | 81 |
| On-eye movement | Yes | Yes | Yes |

Example B-3
Plasma-induced Polymerization of N-vinyl-2-pyrrolidone (Poly-NVP Coating Type 3)

Similarily to Example B-1 the substrates including two lenses from Example A-2, two lenses from Example A-5, two lenses from Example A-8 as well as two pieces of Silastic film (2 cm·1 cm) are, after extraction in isopropanol and drying, placed on the glass holder and positioned in the plasma reactor at a distance of 10 cm from the lower edge of the plasma zone. The reactor is then evacuated to 0.010 mbar and held at this pressure for one hour. The surfaces of the substrates are then activated with argon plasma operated at a plasma power of 170 W, argon flow rate of 20 sccm and a pressure of 0.15 mbar for 1 minute. Afterwards, NVP vapor is introduced into the reactor chamber from the NVP reservoir (maintained at 40° C.) at 0.25 mbar for 2 minutes. The argon flow rate into the plasma zone as well as the argon flow rate through the NVP source (carrier gas) are both set to 10 sccm, the pressure in the reactor adjusted to 0.35 mbar and the RF generator is switched on. The plasma-induced polymerization of NVP is performed at a plasma power of 150 W for 10 minutes. At the end of the reaction period, the base pressure of 0.010 mbar is restored and maintained for 30 minutes. Dry nitrogen is then used to release the internal pressure to atmospheric pressure. After coating of the other side of the substrates by means of the same procedure, the substrates are unloaded from the reactor, extracted in HPLC-water and analyzed by AFM, ATR-FTIR and contact angle measurement. The thickness of the coatings is in the range of 40–50 nm (determined by AFM).

Analysis of the modified substrates:

| Substrate from Example: | A-2 | A-5 | A-8 | Silastic |
|---|---|---|---|---|
| Contact angle [°] Adv./Rec./Hysteresis | 65/39/16 | 59/41/18 | 56/34/22 | 55/39/16 |
| Ionoflux [mm$^2$/min] | $2.8 \cdot 10^{-5}$ | $6.7 \cdot 10^{-5}$ | $3.0 \cdot 10^{-5}$ | — |
| O$_2$D$_k$ [barrer] | 78 | 74 | 81 | — |
| On-eye movement | Yes | Yes | Yes | — |
| Coating thickness [nm] | 46 | 46 | 46 | — |

Determination of the thermooxidative and hydrolytic stability of the coating and its resistance against delamination under shear forces:

According to the procedure outlined above contact lenses are coated with PVP. Atomic Force Microscopy (AFM) and Fourier Transformation Infrared—Attenuated Total Reflection (FTIR-ATR) Spectroscopy are employed for determination of coating uniformity and coating thickness before and after a number of wear and stress tests. FTIR-ATR measurements demonstrate that the coating thickness remain unchanged during autoclaving and no microcrack formation or partial delamination of the coating layer is found by AFM. After 5 repeated swelling (water) and drying cycles, which puts considerable shear forces onto the lens/coating interphase due to different swelling factors, no reduction in coating thickness or partial or patchwise delamination is found by FTIR-ATR or AFM investigations.

Example B-4
Plasma-induced Polymerization of N,N-dimethylacrylamide (Poly-DMA Coating Type 1)

The substrates used in this Example are: two lenses from Example A-2, two lenses from Example A-4, and two pieces of Silastic film (2 cm·1 cm). The substrates are positioned in the reactor at a distance of 16 cm from the lower edge of the plasma zone. The reactor is then evacuated to a pressure of 0.012 mbar and maintained at this pressure for 40 minutes.

The argon plasma gas flow rate into the plasma zone is set to 20 sccm, the pressure in the reactor adjusted to 0.15 mbar and the RF generator is switched on. Plasma discharge at a power of 170 W is maintained for a total period of 1 minute, and then the reactor is again evacuated to a pressure of 0.060 mbar. Afterwards, DMA vapor is introduced into the reactor at 0.25 mbar from the temperated (30° C.) DMA reservoir for 2 minutes. The argon flow rate into the plasma zone as well as the argon flow rate through the DMA reservoir, maintained at 30° C., is then set to 10 sccm, the pressure in the reactor adjusted to 0.30 mbar and the plasma initiated. DMA is polymerized for 10 minutes at a plasma discharge power of 150 W. At the end of the reaction period, the base pressure of 0.012 mbar is restored and maintained for 30 minutes. The reactor pressure is then raised to atmospheric pressure with nitrogen. After coating the other side of the substrates by means of the same procedure, the substrates are washed in distilled water, extracted with HPLC-water and analyzed.

Analysis of the modified substrates:

| Substrate from Example: | A-2 | A-4 | Silastic |
|---|---|---|---|
| Contact angle [°] Adv./Rec./Hysteresis | 61/40/21 | 59/33/26 | 29/20/9 |
| Ionoflux [mm$^2$/min] | — | $6.6 \cdot 10^{-5}$ | — |
| O$_2$D$_k$ [barrer] | — | 74 | — |
| On-eye movement | — | Yes | — |

Example B-5
Plasma-induced Polymerization of N,N-dimethylacrylamide (Poly-DMA Coating Type 2)

Plasma-induced polymerization of DMA on two lenses from Example A-5 and two lenses from Example A-8 is carried out in accordance with Example B-4, but a pressure of 0.35 mbar instead of 0.30 mbar is used for the DMA plasma-induced deposition process.

Analysis of the modified substrates:

| Substrate from Example: | A-5 | A-8 |
|---|---|---|
| Contact angle [°] Adv./Rec./Hysteresis | 64/54/10 | 62/37/25 |
| Ionoflux [mm$^2$/min] | — | $3.3 \cdot 10^{-5}$ |
| O$_2$Dk [barrer] | — | 86 |
| On-eye movement | — | Yes |

Example B-6
Plasma-induced Polymerization of 2-hydroxyethyl Methacrylate (Poly-HEMA Coating)

The substrates used in this Examples are: two lenses from Example A-2, two lenses from Example A-4, two lenses from Example A-8 and two pieces of Silastic film (2 cm·1 cm). The plasma-induced polymerization process with this monomer corresponds to the DMA plasma-induced polymerization process from Example B-5, but instead of a plasma discharge power of 150 W used for DMA polymerization, a power of 110 W is used for the 2-HEMA plasma-induced polymerization.

| Contact angles on the modified substrates: | | | | |
|---|---|---|---|---|
| Substrate from Example: | A-2 | A-4 | A-8 | Silastic |
| Contact angle [°] Adv./Rec./Hysteresis | 78/42/36 | 77/39/38 | 79/48/34 | 78/36/42 |

Example B-7
Plasma-induced Polymerization of N-acryloylmorpholine (Poly-NAM Coating)

Silastic film with a size of 1 cm·2 cm is used as a substrate. Plasma-induced polymerization of NAM is carried out similarity to the plasma-induced polymerization of DMA in Example B-4, but the NAM reservoir temperature is maintained at 50° C. during the entire time of the introduction of NAM vapor into the plasma reactor. Instead of a plasma power of 150 W and a pressure of 0.30 mbar, a plasma power of 240 W and a pressure of 0.25 mbar are applied during this plasma-induced polymerization process.

Contact angles on the Silastic film according to this coating: 24° adv./16° rec./8° hysteresis.

Example B-8
Plasma-induced Polymerization of Methacrylic Acid (Poly-MAA Coating)

The substrates including two lenses from Example A-6, two lenses from Example A-8 and 2 pieces of Silastic film (2 cm·1 cm) are, after extraction in isopropanol, placed on a glass holder and positioned in the plasma reactor at a distance of 16 cm from the lower edge of the plasma zone. After evacuation of the reactor for 40 minutes at 0.010 mbar, argon plasma is used for cleaning and activation of the substrates. Parameters used for argon plasma activation are the following: Argon flow rate: 20 sccm, pressure: 0.15 mbar, plasma power: 170 W and the plasma duration is 1 minute. Then MAA vapor is introduced into the reactor at 0.25 mbar from a cooled (0° C.) MAA reservoir for two minutes. Plasma-induced polymerization of MAA is carried out under the following conditions: Argon flow rate for plasma excitation: 10 sccm, argon carrier gas flow rate for monomer (MAA) transport: 10 sccm, temperature of the monomer evaporation unit: 0° C., pressure: 0.35 mbar, and plasma power: 150 W. Plasma discharge is maintained for a total period of 10 minutes. After this time, the reactor is evacuated and maintained for 30 minutes at a pressure of 0.010 mbar. The internal pressure is then raised to atmospheric pressure using dry nitrogen, the substrates are turned over and the same procedure is used to coat the other side of the substrates.

| Contact angles on the modified substrates: | | | |
|---|---|---|---|
| Substrate from Example: | A-6 | A-8 | Silastic |
| Contact angle [°] Adv./Rec./Hysteresis | 58/19/39 | 65/26/39 | 59/25/24 |

Example B-9
Plasma-induced Polymerization of 4-vinylpyrridine (Poly-4-VPY Coating)

The process described in Example B-8 for plasma-induced polymerization of MAA is repeated for plasma-induced polymerization of 4-VPY on the same substrates.

| Contact angles on the modified substrates: | | | |
|---|---|---|---|
| Substrate from Example: | A-6 | A-8 | Silastic |
| Contact angle [°] Adv./Rec./Hysteresis | 73/37/36 | 62/36/26 | 52/40/12 |

Example B-10
Plasma-induced Polymerization of 2-hydroxyethyl Acrylate (Poly-HEA Coating)

The process described in Example B-8 is repeated for this plasma-induced polymerization on silastic film but the temperature of the monomer evaporation unit is maintained at 25° C. during the entire polymerization process.

III. Preparation of a "Dual-Face" Coated Contact Lens

Example B-11
Plasma-induced Polymerization of Methyl Methacrylate (Poly-MMA Coating) on the One Side and N-vinyl-2-pyrrolidone (Poly-NVP Coating Type 3) on the Other Side of a Substrate The substrates including four lenses from Example A-6 and four pieces of Silastic film (2 cm·1 cm) are, after extraction in isopropanol, placed on a glass holder and positioned in the plasma reactor at a distance of 8 cm from the lower edge of the plasma zone. After evacuation of the reactor for 40 minutes at 0.010 mbar, argon plasma is used for cleaning and activation of the substrates. The parameters used for the argon plasma activation are the following: Argon flow rate: 20 sccm, pressure: 0.08 mbar, plasma power: 170 W and the plasma duration is 1 minute. Then the MMA vapor is introduced into the reactor at 0.25 mbar from a cooled (−35° C.) MMA reservoir for two minutes. Plasma-induced polymerization of MMA is then carried out under the following conditions: Argon flow rate for plasma excitation: 10 sccm, argon carrier gas flow rate for monomer (MMA) transport: 5 sccm, temperature of the monomer evaporation unit: −35° C., pressure: 0.35 mbar, and plasma power: 150 W. Plasma discharge is maintained for a total period of 10 minutes. After this time, plasma discharge is interrupted, the reactor evacuated and maintained for 30 minutes at a pressure of 0.010 mbar. The internal pressure is then brought to atmospheric pressure by using dry nitrogen, the substrates are turned over and the procedure described in Example B-3 is used to coat the other side of the substrates. The structure of both coatings is determined by ATR-FTIR spectroscopy.

IV. Preparation of a Laminate Coating

Example B-12

Plasma-induced Polymerization of N,N-dimethylacrylamide (Poly-DMA Coating on Substrates Already Coated with Poly-NVP3 Coating Two lenses from Example A-4, two lenses from Example A-6 and two pieces of Silastic film (2 cm·1 cm) are coated with Poly-NVP3 coating in accordance with Example B-3, but instead of 10 minutes, coating time is only 5 minutes. Thereafter, the substrates are not unloaded from the reactor, further coated with Poly-DMA in accordance with Example B-4, however, also only for 5 minutes. Both coatings are clearly detectable on substrate surfaces by ATR-FTIR spectroscopy.

| Contact angles on the modified substrates: | | | |
|---|---|---|---|
| Substrate from Example: | A-4 | A-6 | Silastic |
| Contact angle [°] Adv./Rec./Hysteresis | 61/40/21 | 59/33/26 | 49/28/21 |

V. Preparation of a Copolymer Coating

Example B-13

Plasma-induced Polymerization of a Mixture of N,N-dimethylacrylamide and N,N-dimethylaminoethyl Methacrylate (Poly-DMA-poly-DMAEMA Coating)

Two lenses from Example A-4, two lenses from Example A-6 and two pieces of Silastic film (2 cm·1 cm) are coated in accordance with Example B-4, but instead of DMA, a mixture of DMA and DMAEMA in a ratio of 1:1 is used as a monomer source for the plasma-induced grafting.

| Contact angles on the modified substrates: | | | |
|---|---|---|---|
| Substrate from Example: | A-4 | A-6 | Silastic |
| Contact angle [°] Adv./Rec./Hysteresis | 61/49/12 | 67/43/24 | 69/38/31 |

VI. Preparation of a Crosslinked Copolymer Coating

Example B-14

Plasma-induced Polymerization of a Mixture of 2-hydroxyethyl Methacrylate (80%) and Ethylene Glycol Dimethacrylate (20%) (Crosslinked Poly-HEMA Coating)

Two lenses from Example A-4, two lenses from Example A-6 and two pieces of Silastic film (2 cm·1 cm) are coated in accordance with Example B-6, but instead of HEMA, a mixture of HEMA and EGDMA in a volume ratio of 4:1 is used as a monomer source for the plasma-induced grafting.

| Contact angles on the modified substrates: | | | |
|---|---|---|---|
| Substrate from Example: | A-4 | A-6 | Silastic |
| Contact angle [°] Adv./Rec./Hysteresis | 71/49/22 | 77/38/39 | 79/38/41 |

VII. Determination of the Repeating Units in the Plasma-induced Coatings

Example C-1

Establishment of a Calibration Curve Related to FTIR-ATR Absorption of Repeating Poly-vinyl-pyrrolidone Structural Units In order to quantify the extent of the vinylpolymer structures within the coatings prepared by after-glow graft polymerization of N-vinyl pyrrolidone (NVP) with 4-vinyl pyridin (NVPy), a number of regular copolymers of NVP and NVPy are prepared following standard polymerization procedures (10% solution in ethanol, AIBN ($\alpha,\alpha'$-Azoisobutyronitrile) as catalyst, 70° C., 8 hrs reaction time).

The PVP content of these copolymers are determined by $^1$H-NMR. Coatings of copolymers are then prepared by spin-casting of corresponding ethanol solutions on 40 µm thick polypropylene (PP) film. The thickness of a copolymer coating is set to 120–140 nm. FTIR-ATR spectra of the copolymer coatings on PP are taken by using a Germanium crystal. Extinctions of the carbonyl groups of the PVP segments at 1670 cm$^{-1}$ and of the —CH-groups of the underlying PP films are determined. For three measurements on each copolymer film the relative extinctions $E_1/E_2$ are calculated. The average values for $E_1/E_2$ can then beplotted versus the PVP contents of the copolymers.

Table I shows the data obtained by the procedure above. Accordingly, the PVP content in weight % can be correlated with the relative extinction ($E_1/E_2$).The linear regression, which results from said correlation reads as follows:

$$y=0.4913x-33.714$$

wherin y is the relative extinction $E_1/E_2$, and x represents the PVP content in weight %.

Said regression is used infra (Example C-2) for the quantitative determination of the repeating PVP-units in the coating obtained in the plasma induced after-glow coating process.

TABLE I

| % PVP by $^1$H-NMR | $E_1$ of PVP C=O at 1670 cm$^{-1}$ | $E_2$ of PP (—CH—) at 1600 cm$^{-1}$ | $E_1/E_2$ | Average Value $E_1/E_2$ |
|---|---|---|---|---|
| 80 | 0.2648 | 0.04147 | 6.385 | 6.4598 |
| 80 | 0.2639 | 0.04018 | 6.568 | |
| 80 | 0.2983 | 0.04642 | 6.426 | |
| 91 | 0.3545 | 0.03795 | 9.341 | 9.4069 |
| 91 | 0.3184 | 0.03419 | 9.313 | |
| 91 | 0.2429 | 0.02539 | 9.567 | |
| 95 | 0.2986 | 0.02455 | 12.163 | 12.3541 |
| 95 | 0.2531 | 0.01965 | 12.880 | |
| 95 | 0.4209 | 0.03502 | 12.019 | |
| 100 | 0.201 | 0.01202 | 16.722 | 17.0443 |

TABLE I-continued

| % PVP by $^1$H-NMR | $E_1$ of PVP C=O at 1670 cm$^{-1}$ | $E_2$ of PP (—CH—) at 1600 cm$^{-1}$ | $E_1/E_2$ | Average Value $E_1/E_2$ |
|---|---|---|---|---|
| 100 | 0.2129 | 0.01272 | 16.777 | |
| 100 | 0.2243 | 0.01272 | 17.634 | |

Example C-2
Determination of the Content in PVP Structural Elements in After-glow Plasma Grafted PVP Coatings.

According to the procedures outlined in Examples B-1 and B-3 plasma-induced PVP coatings are prepared on 40 μm thick PP films. Data on the FTIR-ATR extinctions of the PVP segments within the coating materials are determined as described in the foregoing example. Using the above calibration curve (see Example C-1), the percentage of the PVP repeating units is calculated on the basis of their relative extinctions. Consequently, the PVP content retained in the plasma-induced after-glow process is 97.9, 88.7 and 87.4% respectively (see Table II).

TABLE II

| PVP coating from Example No. | Coating Thickness by AFM, [nm] | Relative Extinction $E_1/E_2$ | PVP content in (%) calculated from calibration curve |
|---|---|---|---|
| B-3 | 50–60 | 14.430 | 97.9 |
| B-1 | 120–140 | 9.88 | 88.7 |
| B-1 | 120–140 | 9.21 | 87.4 |

Prolonged exposure times, which would be needed for thicker coatings (120–140 nm), reduce the content of PVP repeating units.

What is claimed is:

1. An article selected from the group consisting of a contact lens, an intraocular lens and a lenticular corneal implant (artificial cornea) comprising a substrate which is at least partially coated with a polymeric coating, which is obtained by after-glow plasma-induced polymerization of a polymerizable unsaturated compound (monomer) on the substrate, wherein the substrate is positioned at a distance of 4 to 40 cm and the monomer inlet at a distance of 3 to 35 cm downstream outside the plasma zone, wherein the plasma is a pulsed plasma, and wherein the polymer chains of the coating are composed of 2% to 30% of repeating units which are sites of cross-linkage and/or covalent bonding to the substrate.

2. Article of claim 1, wherein 2% to 24% of the repeating units represent sites of cross-linkage and/or covalent bonding to the substrate.

3. An article according to claim 1, wherein the substrate is an organic polymer.

4. An article according to claim 1, wherein the polymerizable unsaturated compound (monomer) is a vinyl compound.

5. An article according to claim 4, wherein the vinyl compound is selected from N-vinyl pyrrolidone, N,N-dimethylacrylamide, hydroxyethyl methacrylate, methyl methacrylate, dimethylaminoethyl methacrylate, (meth-)acrylic acid, 2-hydroxyethyl acrylate, vinylpyridine, methyl vinyl ether, ethyl vinyl ether, methoxyethyl vinyl ether, ethylene glycol dimethacrylate, N-acryloylmorpholine or mixtures thereof.

6. An article according to claim 1, wherein the monomer is N-vinyl pyrrolidone.

7. An article according to claim 1, wherein at least two monomers are used for forming the polymeric coating.

8. An article according to claim 1, wherein an additional crosslinking monomer is used for forming the polymeric coating.

9. An article according to claim 1, wherein the polymeric coating is a laminate coating produced by a sequential polymerization of at least two polymerizable unsaturated compounds optionally together with a crosslinking monomer.

10. An article according to claim 1, wherein the polymeric coating has a thickness of 1 to 5000 nm.

11. An article according to claim 1, wherein the polymeric coating is in the form of a pattern.

12. An article according to claim 1, which is an extended-wear contact lens.

13. The contact lens according to claim 12 wherein said lens has a polymeric coating on the lens and said lens comprising polysiloxane and/or perfluoroalkyl groups.

14. The lens of claim 13, wherein the coating exhibits a wettability, expressed as the contact angle with water of ≦75° advancing, <65° receding and <46° hysteresis.

15. The contact lens of claim 12, wherein the front and the back surface of said lens are each coated with a different polymer.

* * * * *